United States Patent
Madsen et al.

(10) Patent No.: US 10,942,238 B2
(45) Date of Patent: Mar. 9, 2021

(54) SYNCHRONIZATION DEVICES AND METHODS FOR SYNCHRONIZING IMAGING SYSTEMS AND STIMULATION SYSTEMS

(71) Applicant: LVIS Corporation, Palo Alto, CA (US)

(72) Inventors: Michael Madsen, Santa Clara, CA (US); Zhongnan Fang, Santa Clara, CA (US); Jin Hyung Lee, Palo Alto, CA (US)

(73) Assignee: LVIS Corporation, Palo Alto, CA (US)

( * ) Notice: Subject to any disclaimer, the term of this patent is extended or adjusted under 35 U.S.C. 154(b) by 74 days.

(21) Appl. No.: 16/469,016

(22) PCT Filed: Dec. 12, 2017

(86) PCT No.: PCT/US2017/065733
§ 371 (c)(1),
(2) Date: Jun. 12, 2019

(87) PCT Pub. No.: WO2018/111826
PCT Pub. Date: Jun. 21, 2018

(65) Prior Publication Data
US 2019/0317170 A1    Oct. 17, 2019

Related U.S. Application Data

(60) Provisional application No. 62/433,026, filed on Dec. 12, 2016.

(51) Int. Cl.
*G01R 33/561*    (2006.01)
*A61N 1/05*    (2006.01)
(Continued)

(52) U.S. Cl.
CPC .......... *G01R 33/5613* (2013.01); *A61N 1/05* (2013.01); *A61N 1/08* (2013.01); *G01R 33/5676* (2013.01)

(58) Field of Classification Search
CPC ........ A61N 1/05; A61N 1/08; A61N 1/36128; G01R 33/05; G01R 33/5676; G01R 33/28;
(Continued)

(56) References Cited

U.S. PATENT DOCUMENTS

2006/0004422 A1*    1/2006    De Ridder .......... A61N 1/0531
                                                              607/45
2011/0257509 A1    10/2011    Olsen et al.
(Continued)

FOREIGN PATENT DOCUMENTS

WO    2018111826 A1    6/2018

OTHER PUBLICATIONS

International Search Report and Written Opinion received for PCT Appl. No. PCT/US2017/065733, dated Mar. 7, 2018.
(Continued)

*Primary Examiner* — Susan S Lee
(74) *Attorney, Agent, or Firm* — Dorsey & Whitney LLP (57) ABSTRACT

Examples described herein may provide for pre-triggering imaging scans (e.g. fMRI scans) using an electronic timer synchronized to a stimulation system.

21 Claims, 6 Drawing Sheets

(51) Int. Cl.
   *A61N 1/08* (2006.01)
   *G01R 33/567* (2006.01)
(58) Field of Classification Search
   CPC ... G01R 33/4806; A61B 5/4064; A61B 5/055;
   A61B 5/7292
   See application file for complete search history.

(56) References Cited

U.S. PATENT DOCUMENTS

2014/0018882 A1* 1/2014 Wilke ............... A61N 1/36103
   607/45
2014/0364721 A1 12/2014 Lee et al.
2015/0223721 A1* 8/2015 De Ridder ........... A61N 1/0531
   600/411

OTHER PUBLICATIONS

PCT Application No. PCT/US2017/065733, entitled 'Synchronization Devices and Methods for Syncrhonizing Imaging Systems and Stimulation Systems', dated on Dec. 12, 2017, pp. all.
Extended European Search Report for EP Application No. 17881833.2, dated Sep. 7, 2020.
Younce, John R. et al., "Deep Brain Stimulation With Simultaneous fMIR in Rodents", J. Vis. Exp. (84), e5127, doi: 10.3791/51271, Feb. 15, 2014, 1-7.
Zhao, F. et al., "Pain fMRI in Rat Cervical Spinal Cord: An Echo Planat Imaging Evalution Of Sensitivity of BOLD and Blood Volume-Weighted fMRI", NeuroImage 44 (2009), 2008, 349-362.

* cited by examiner

SYNCHRONIZATION DEVICES AND METHODS FOR SYNCHRONIZING IMAGING SYSTEMS AND STIMULATION SYSTEMS

CROSS-REFERENCE TO RELATED APPLICATIONS)

This application is a 35 U.S.C. § 371 National Stage Application of PCT Application No. PCT/US2017/065733, filed Dec. 12, 2017, which claims the benefit under 35 U.S.C. § 119 of the earlier filing date of U.S. Application Ser. No. 62/433,026, filed Dec. 12, 2016 the entire contents of which are hereby incorporated by reference, in their entirety, for any purposes.

TECHNICAL FIELD

Examples described herein relate to magnetic resonance imaging systems (MRI systems). Examples of synchronizing MRI systems with stimulation systems (e.g. implantable stimulators) are described.

BACKGROUND

Functional Magnetic Resonance Imaging (fMRI) may require several repeated scans to enter a steady state. When fMRI is triggered by a periodic implanted stimulator, there may be a waste of a complete stimulation cycle while the fMRI system attains a steady state. This not only increases the scan time, but may also reduce the patient comfort and increase susceptibility of motion artifacts.

SUMMARY

Examples described herein include methods relating to magnetic resonance imaging systems. An example method may include initiating a functional magnetic resonance imaging scan (an fMRI scan) of a patient with a functional magnetic resonance imaging system (an fMRI system) at an initiation time prior to a stimulation time when the patient is stimulated by an implanted stimulator. The implanted stimulator may be configured to stimulate the patient every period. A duration between the initiation time and the stimulation time may be sufficient for the fMRI system to achieve a steady state. The method may further include initiating another fMRI scan of the patient one period after the initiation time.

In some examples, the method may further include performing dummy scans with the fMRI system at a time between the initiation time and the stimulation time.

In some examples, the one period after the initiation time is prior to a second stimulation time when the patient is again stimulated by the implanted stimulator.

In some examples, the method may further include performing dummy scans with the fMRI system at a time between the one period after the initiation time and the second stimulation time.

In some examples, the method may further include receiving indication of an initial stimulation time from the implanted stimulator and calculating, using an electronic timer, the initiation time at least in part by adding the period to the initial stimulation time and subtracting a settling time during which the fMRI is configured to achieve the steady state.

In some examples, the method may further include providing a trigger signal from the electronic timer to the fMRI system at the initiation time.

In some examples, the method may further include counting, with the electronic timer, the period, and providing another trigger signal from the electronic timer to the fMRI system at the one period after the initiation time.

Examples described herein include devices related to magnetic resonance imaging systems. In some examples, a device may include an input configured to receive an indication of stimulation initiation from an implanted stimulator, the implanted stimulator configured to provide stimulation every period. The device may further include synchronization circuitry configured to calculate an initial time of scan initiation at least in part by adding the period to a time the indication of stimulation initiation was received and subtracting a settling time during which a scanning system is configured to attain steady state. The device may further include trigger circuitry configured to provide a trigger to the scanning system to initiate a scan at the initial time.

In some examples, the synchronization circuitry is further configured to calculate a next time of scan initiation at least in part by adding the period to the initial time. In some examples, the trigger circuitry is further configured to provide another trigger to the scanning system at the next time.

In some examples, the synchronization circuitry is provided in a field programmable gate array (FPGA) device.

In some examples, the device may include a display configured to display a remaining time until the initial time.

In some examples, the device is configured to implement a state machine, and wherein a first state includes a standby state, the device further includes a second input configured to receive an indication to exit standby state. In some examples, the synchronization circuitry is configured to calculate the initial time responsive to receipt of the indication of stimulation when the device has exited the standby state.

In some examples, the second input includes a user accessible switch.

In some examples, the device includes a second state including an initial trigger calculation state during which the synchronization circuitry is configured to calculate the initial time. In some examples, the device includes a third state including a repetitive trigger state during which the synchronization circuitry is configured to calculate next trigger times by adding the period to a previous trigger time.

In some examples, the device includes a memory configured to store the period.

Examples described herein include systems related to magnetic resonance imaging systems. In some examples, a system includes a functional magnetic resonance imaging system (an fMRI system), the fMRI system configured to provide fMRI scans of a patient. The system may include a stimulation system configured to stimulate the patient. The system may include a synchronization device, the synchronization device configured to trigger the fMRI system to initiate at least one of the fMRI scans at a time prior to simulation of the patient by the stimulation system, such that the fMRI system attains steady state prior to the stimulation of the patient by the stimulation system.

In some examples, the fMRI system is configured to provide at least one dummy scan prior to attaining the steady state.

In some examples, the synchronization device is configured to receive an initial indication of stimulation from the stimulation system. In some examples, the synchronization device is configured to determine a first trigger time by adding a period of the simulations provided by the stimulation system to a time of the initial indication and subtracting a settling time during which the fMRI system is configured to attain the steady state.

In some examples, the synchronization device is configured to provide a trigger signal to the fMRI system to initiate a scan at the first trigger time.

In some examples, the synchronization device is configured to determine subsequent trigger times by adding multiples of the period to the first trigger time.

In some examples, wherein the synchronization device is configured to provide trigger signals to the fMRI system to initiate scans at the subsequent trigger times.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known imaging system components, imaging techniques, circuits, control signals, timing protocols, and software operations have not been shown in detail in order to avoid unnecessarily obscuring the described embodiments of the invention.

Examples described herein may provide for pre-triggering imaging scans (e.g. fMRI scans) using an electronic timer synchronized to a stimulation system.

Figure 1:
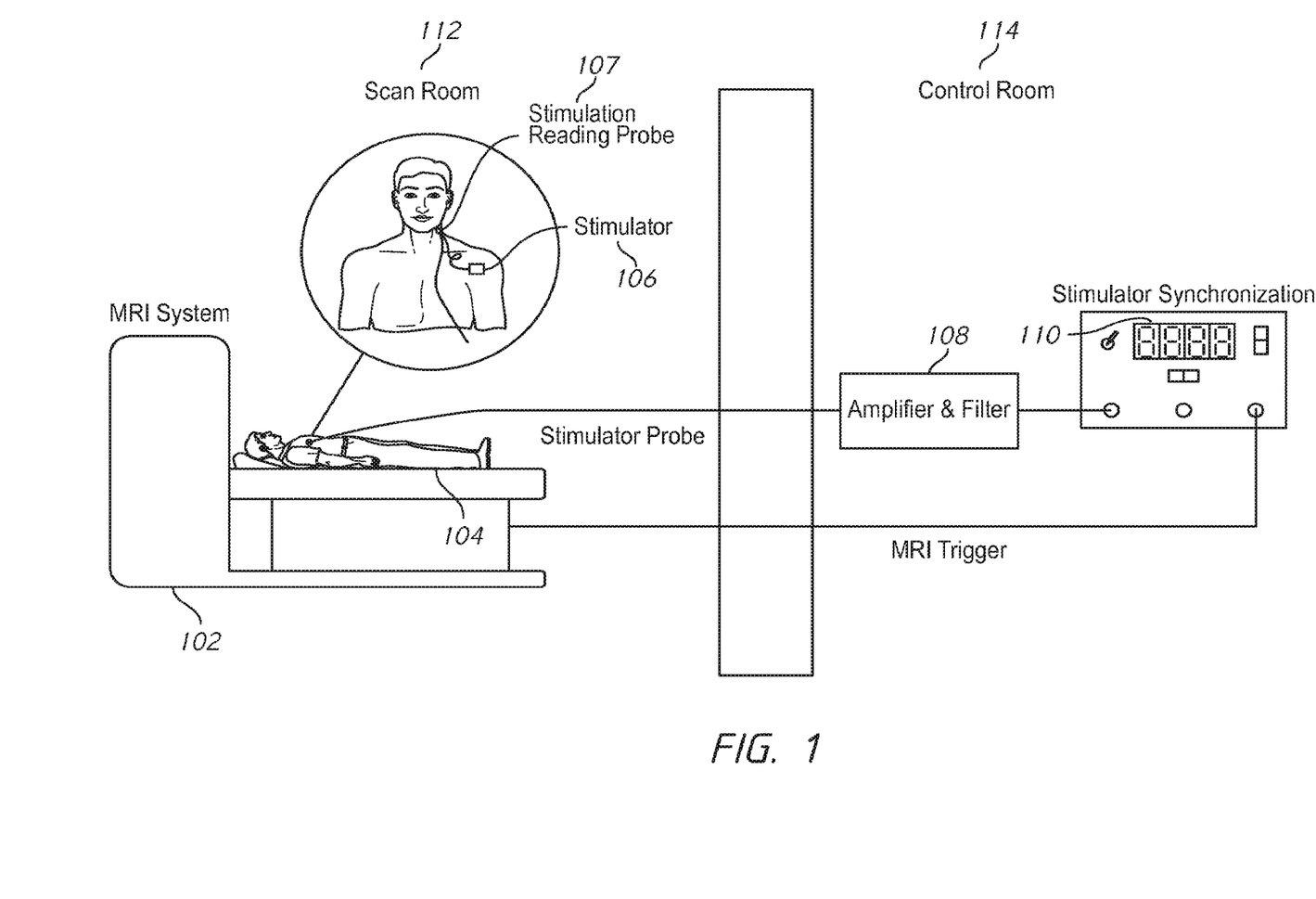
FIG. 1 is a schematic illustration of a system arranged in accordance with examples described herein.

FIG. 1 is a schematic illustration of a system arranged in accordance with examples described herein. The system of FIG. 1 includes a functional magnetic resonance system (fMRI system 102), patient 104, implanted stimulator 106, stimulation reading probe 107, amplifier & filter 108, synchronization device 110, scan room 112, and control room 114. Generally, a patient 104 may be positioned for analysis by the fMRI system 102 (e.g. placed on a table or other receiving surface of the fMRI system 102). The fMRI system 102 and patient 104 may be located in a scan room 112. The patient 104 may have an implanted stimulator 106. The implanted stimulator 107 and the stimulation reading probe 106 may be on any part of the body. The stimulation reading probe 106 may be outside of the body in some examples, while the implanted stimulator 107 may be inside the body. The stimulation reading probe 107 may be in communication with amplifier & filter 108 and/or synchronization device 110. For example, the stimulation reading probe 107 may provide an indication of stimulation initiation to the amplifier & filter 108 and/or synchronization device 110. The synchronization device 110 may be in communication with the fMRI system 102. The synchronization device 110 may provide a trigger to the fMRI system 102 to initiate a scan. The amplifier & filter 108 and/or synchronization device 110 may be located in control room 114.

Examples of systems described herein may include magnetic resonance imaging (MRI) systems. A functional magnetic resonance imaging system (fMRI system) is shown in FIG. 1 and examples of fMRI systems are described herein. fMRI systems generally refer to system employing neuroimaging procedures using MRI technology to measure brain activity by detecting changes in blood oxygen level. Other MRI systems and/or techniques may also or instead be used with examples described herein, including but not limited to MRI systems or diffusion MRI systems. MRI systems, including fMRI systems, may include a variety of components including, but not limited to magnets, controllers, hardware, circuitry, firmware, software, displays, computing systems, or combinations thereof. The MRI systems described herein may generally be used to provide MRI scans (e.g. fMRI systems may be used to provide fMRI scans) of a patient, such as the patient 104 in FIG. 1.

An MRI scan, or fMRI scan, may generally refer to an image, or data from which an image may be generated, of a patient and/or portion of a patient. The scan may include data responsive to one or more magnetic fields and/or radiofrequency (RE) pulses that may be provided proximate the patient and/or portions of the patient. Scans may provide, for example, a series of magnetic fields and/or RF pulses sufficient to obtain data and/or an image of desired portions of a patient. Generally, a number of scans may be required to obtain an image of a patient or portion of patient. For example, 5 to 10 minutes of scans may be used in some examples. Overall, in some examples, it may take 2 to 3 hours or longer to obtain the multitude of images desired from a scanning session. Other times may be used in other examples. Patients described herein, such as the patient 104 may be human, animal, cadaver, or other tissue specimens. Either adults or children may be used as patients described herein. In some examples, an entire patient may be scanned using techniques described herein (e.g. whole-body scanning may be used). In some examples, one or more portions of a patient may be scanned using techniques described herein (e.g. brain, lung, liver, other organ).

Prior to receiving usable data from a scan, MRI systems (including fMRI system 102) may have or require a settling time during which the MRI system has not attained steady state. Some amount of scan activity (e.g. application of gradient magnetic fields and/or RF pulses) may be needed prior to attaining steady state. This scan activity may be referred to as 'dummy scans' or 'pre-steady-state scans'. Data may or may not be collected from the MRI system during these dummy scans, but generally the data collected during dummy scans may not be considered reliable or usable data. Dummy scans may be desirable, for example, because the system may not have attained steady state at an initial scan. For example, a first application of gradient magnetic fields and/or RF pulses may perturb the system including the patient. At the time of a second scan, the system may not have relaxed and may be at a different state on initiation of the second scan. After some amount of dummy scans, the system may generally be at a steady state prior to initiation of each scan. Accordingly, the fMRI system 102 may provide at least one dummy scan prior to attaining the steady state. In some examples, other numbers of dummy scans may be used, including, but not limited to 2, 3, 4, 5, 6, 7, 8, 9, or 10 dummy scans.

A stimulation system may be used to stimulate the patient, such as the patient 104. The stimulation system may include implanted stimulator 106. Examples of stimulation systems include systems that provide stimulation, such as electrical stimulation, to a patient. Stimulation systems may provide a stimulation such that the MRI system, such as fMRI system 102, may provide scans of the patient responsive to stimulation by the stimulation system. Stimulation systems may include implanted stimulators, which may include one or more electrodes which may be implanted in, placed on, and/or positioned in proximity to the patient. For example, the implanted stimulator 106 may include an electrode implanted in a patient's brain. Stimulation systems may include electronics and/or other components for generating and providing stimulation, including, but not limited to, power sources, conditioning circuitry, and/or communication components.

During operation, the stimulation system may stimulate the patient periodically, with the stimulations occurring every period of time. In some examples, the period may be regular. In other examples, the period may be irregular (e.g. some stimulations may be closer together than others).

Examples described herein may include a synchronization device, such as synchronization device 110. During operation, the synchronization device 110 may provide a trigger signal to the MRI system (e.g. FMRI system 102) which may trigger the MRI system to initiate an fMRI scan at a time prior to stimulation of the patient by the stimulation system, such as by implanted stimulator 106. The trigger may occur prior to stimulation of the patient such that the MRI system (e.g. the fMRI system 102) may attain steady state prior to the stimulation of the patient by the stimulation system (e.g. including implanted stimulator 106). Accordingly, the synthronization device may initiate scanning by the MRI system such that any needed dummy scans are completed by the time the stimulation system stimulates the patient. In this manner, wasted data from dummy scans may be reduced and/or avoided after stimulation.

Synchronization devices described herein, such as the synchronization device 110, may receive an indication of stimulation (e.g. an initial indication of stimulation) from the stimulation system, which may include implanted stimulator 106. The stimulation system may provide a designated signal indicative of stimulation to the synchronization device in some examples. In some examples, the indication of stimulation may be a signal occurring as part of the regular course of operation of the stimulation system. For example, a voltage on the implanted stimulator 106 may transition beyond a threshold voltage at a start of stimulation, and the increased magnitude may be detected by the synchronization device 110, providing an indication of stimulation. The amplifier & filter 108 may be provided and used to manipulate a signal generated by the stimulation system, such as the implanted stimulator 106, and provide a signal indicative of stimulation to the synchronization device 110. In some examples, the amplifier & filter 108 may be integrated into the synchronization device 110. Communication between the stimulation system and the synchronization device may be wired or wireless.

The synchronization device may utilize a period of stimulations by the stimulation system and a settling time of the MRI system, such as the fMRI system 102, to determine a trigger time, e.g. a first trigger time, at which to provide a trigger signal. Data indicative of the period or periods of stimulations by the stimulation device may be stored in a location accessible to the synchronization device, such as the synchronization device 110, e.g. the data may be programmed in the synchronization device. In some examples, data indicative of the period or periods of stimulations by the stimulation system may be provided to the synchronization device by the stimulation system and/or the MRI system. Data indicative of the settling time of the MRI system, e.g. fMRI system 102, may be stored in a location accessible to the synchronization device. For example, the data may be programmed in the synchronization device. In some examples, data indicative of the settling time of the MRI system may be provided to the synchronization device by the stimulation system and/or the MRI system. In some examples, the synchronization device may detect the settling time by observing one or more characteristics of the patient and/or MRI system indicative of steady state operation.

A first trigger time may be calculated by the synchronization device 110 by adding a period of the stimulations to be provided by the implanted stimulator 106 to a time of the initial indication of stimulation and subtracting a settling time during which the fMRI system 102 may attain a steady state. For example, the synchronization device may receive an initial indication of stimulation from the stimulation system, such as implanted stimulator 106. The synchronization device may be used to initiate a next MRI scan at a trigger time prior to the next anticipated stimulation time to allow for dummy scans to be completed prior to the next anticipated stimulation. The next anticipated stimulation may occur a period after the initial stimulation. Accordingly, the synchronization system may provide a trigger such that scanning begins at a trigger time which is a settling time before the period after the initial stimulation.

A trigger signal may be provided by the synchronization device, e.g. synchronization device 110 to the MRI system, e.g. fMRI system 102. The trigger signal may be provided using wired or wireless communication. The trigger signal may be provided such that the fMRI system 102 initiates a scan at the trigger time. In some examples, the trigger may be provided at a time before the trigger time to account for any communication delay between the synchronization device 110 and the fMRI system 102.

Following the initial stimulation and trigger signal, subsequent trigger times may be determined by the synchronization device by adding a next period to the first trigger time. In this manner, subsequent scans may be started by the fMRI system 102 at sufficient times prior to subsequent stimulations by implanted stimulator 106 to allow the fMRI system 102 to achieve steady state prior to stimulation. In some examples, the periods may be regular, and accordingly, multiples of the period may be added to the first trigger time to determine subsequent trigger times. In some examples, the periods may not be regular and different period times may be added to one trigger time to determine a next trigger time. The synchronization device may provide trigger signals to the MRI system to initiate scans at the subsequent trigger times.

Any number of periods of stimulation may be used in examples described herein including 1, 2, 4, 5, 6, 7, 8, 9, 10, or another number of stimulation periods may be used in some examples. In some examples, after an initial trigger signal, images may be acquired over multiple periods (e.g. 5, 6, 7, 8, 9, 10) periods prior to triggering the scanning system again. Generally, synthronization systems described herein may provide a trigger signal every period in some examples, but trigger signals after a first period may not interrupt the scanning system in some examples.

In FIG. 1, the fMRI system 102 and patient 104 are shown in a scan room 112 while the synchronization device 110 is shown in a control room 114. This may be a common configuration of components, for example, where the synchronization device 110 may be located in a separate room from the fMRI system 102, which may generate strong magnetic and/or RF fields, and an operator may be in another room, such as control room 114. However, a separate room is not required and, in some examples, the synchronization device 110 may be located in a same room as the fMRI system 102.

Figure 2A:
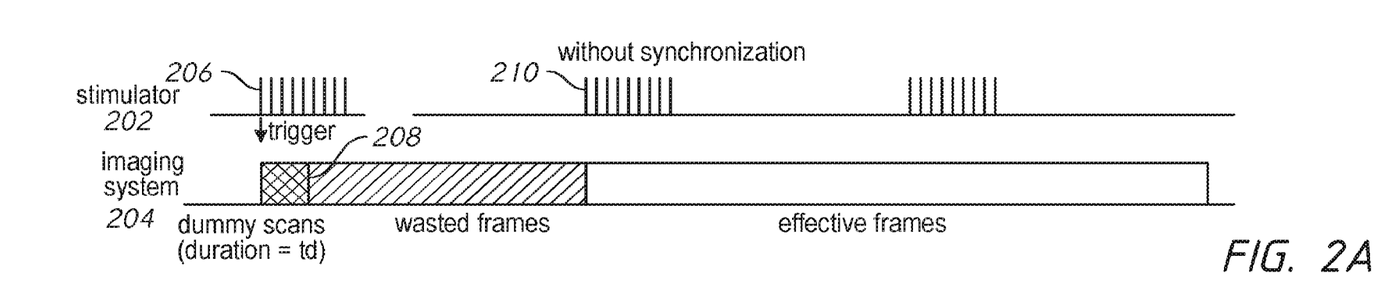
FIGS. 2A-C are timing diagrams illustrating operation of an MRI system and a stimulation system.
Figure 2B:
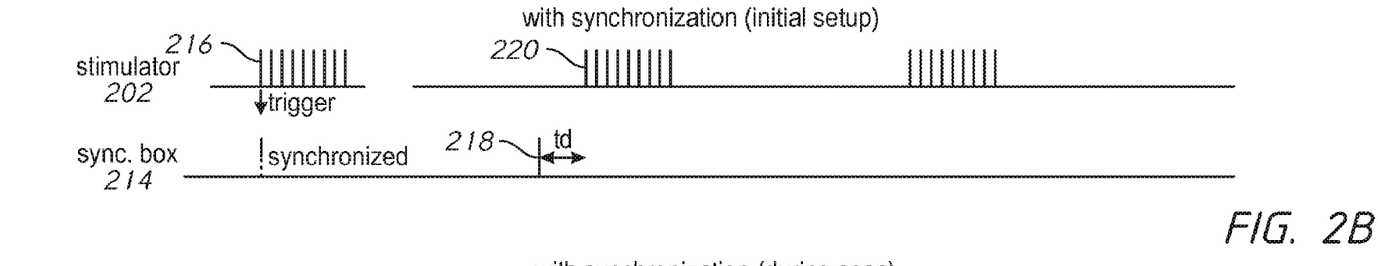
Figure 2C:
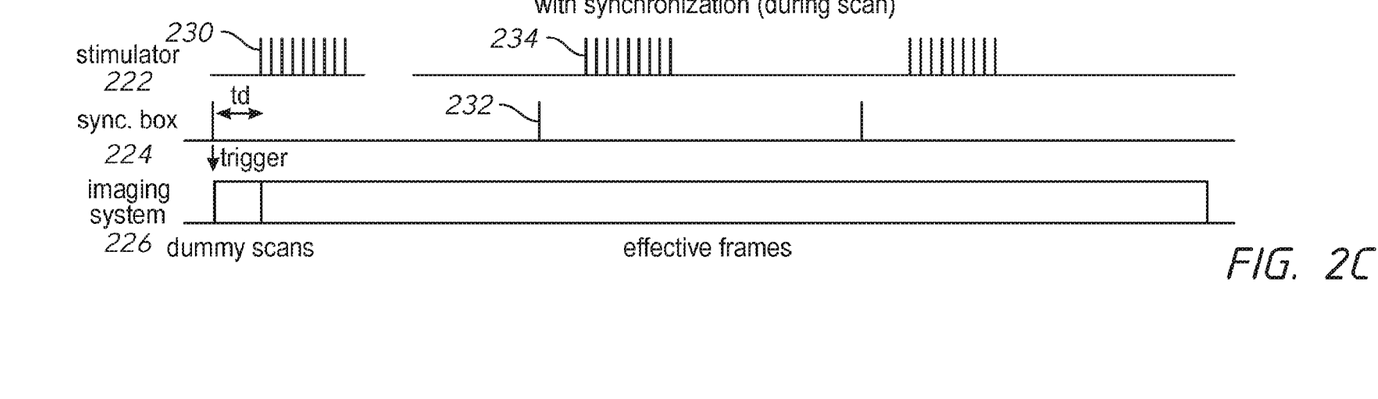

FIGS. 2A-2C are timing diagrams illustrating operation of an MRI system and a stimulation system, FIG. 2A illustrates operation of an MRI system without use of synchronization devices or techniques described herein. FIG. 2A accordingly illustrates problems which may occur without use of synchronization devices and/or techniques described herein, such as the synchronization device 110 of FIG. 1. In FIG. 2A, signal timing is shown for stimulation system 202 and fMRI system 204. At time 206, a stimulation system begins stimulation of a patient (for example, the implanted stimulator 106 may begin stimulation of patient 104 in FIG. 1). The stimulation is shown as a series of spikes. For example, stimulation may include delivering a series of current and/or voltage spikes using implanted stimulator 106. At time 206, when the stimulation begins, the fMRI system 204 begins taking dummy scans. Those scans are occurring during the stimulation time (through time 210, and accordingly, the frames of data collected through the next stimulation time, shown as through time 210 in FIG. 2A, are wasted in that the data is not considered reliable and/or usable. Once a next stimulation occurs, at time 210 in FIG. 2A, the frames are usable. Note that one period of fMRI data is lost, and this will recur for every sequence of fMRI scan that is used. Multiple sequences of fMRI scans may be used in some examples, resulting in multiple unusable frames of data. For example, multiple stimulations may be captured per fMRI scan. A first stimulation per scan may be lost in some examples while synchronization is established, but all (or more) data may be available during subsequent stimulations. For example, referring to FIG. 2A, some data associated with stimulation 216 may not be usable owing to initial setup of a synchronization system, but during other stimulation sequences (e.g. stimulation 220, stimulation 230), all data (or more data) may be usable.

FIG. 2B illustrates an example of initial signal timing during use of synchronization devices and/or synchronization techniques described herein. FIG. 2B shows signals for stimulation system 212 and synchronization device 214. At time 216, a first trigger time, the stimulation system 212 has a first stimulation, shown in FIG. 2B as a sequence of spikes. When the first stimulation begins, an initial indication of stimulation is provided to the synchronization device 214. The synchronization device 214 may accordingly calculate a trigger time by adding a period to the time of initial stimulation and subtracting a settling time for the MRI system. At the trigger time, time 218, the synchronization device 214 provides a trigger signal to an MRI system to begin a scan such that the MRI system reaches steady state by the time of the next stimulation, time 220 in FIG. 2B.

FIG. 2C illustrates an example of signal timing during use of synchronization devices and/or synchronization techniques described herein after initial synchronization, as in FIG. 2B. FIG. 2C illustrates timing diagrams for stimulation system 222, synchronization device 224, and MRI system 226. At time 228, the synchronization device 224 may provide a tugger signal at a time sufficiently prior to a time of stimulation, such as the time 230. The trigger signal at time 228 causes the MRI system 226 to initiate scanning.

The dummy scans may be complete by the time of stimulation at time 230, and accordingly effective MRI data is collected. The synchronization device 224 may provide a next trigger signal at a time 232, a settling time prior to a next stimulation time 234. Accordingly, trigger signals may be provided periodically prior to next stimulations by the stimulation system.

Figure 3:
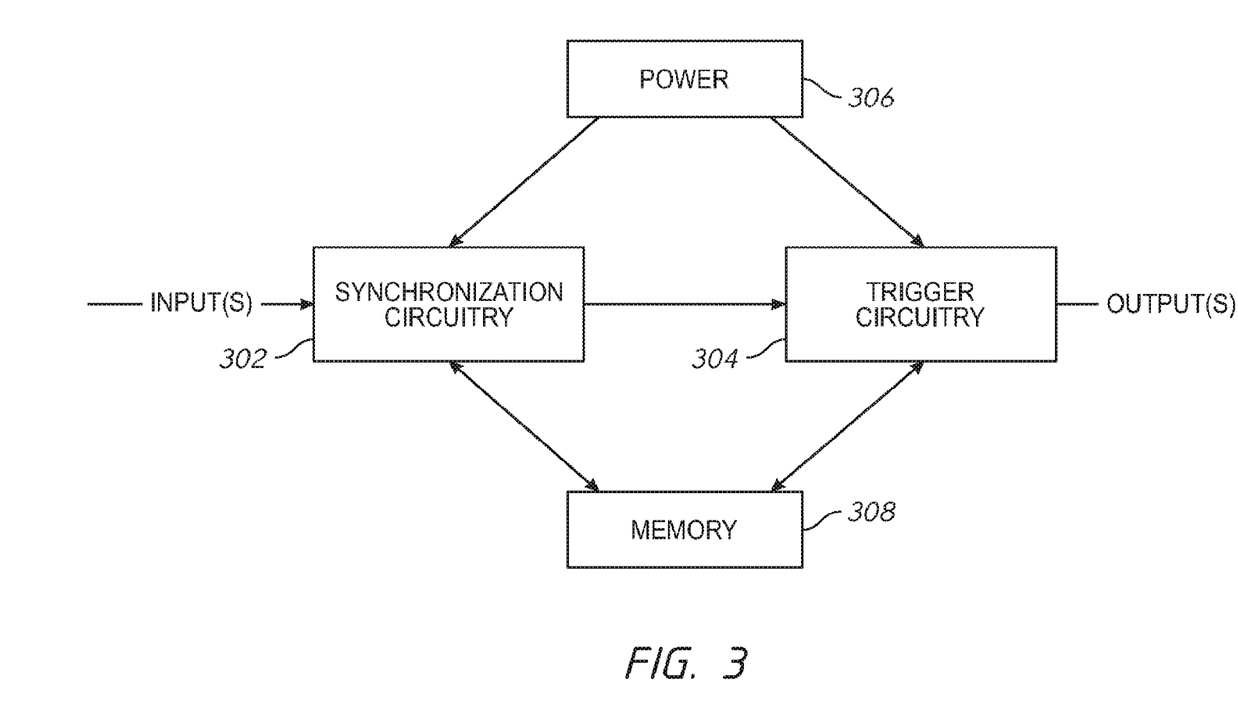
FIG. 3 is a schematic illustration of a synchronization device arranged in accordance with examples described herein.

FIG. 3 is a schematic illustration of a synchronization device arranged in accordance with examples described herein. The synchronization device includes synchronization circuitry 302, trigger circuitry 304, power 306, and memory 308. Additional components and/or fewer components may be present in other examples.

The synchronization circuitry 302 and trigger circuitry 304 are shown as separate boxes in FIG. 3, however, it is to be understood that these components may be combined in some examples. Moreover, while described as circuitry in some examples, in other examples, the circuitry may be implemented at least partially in software—e.g. using one or more processors and computer readable media encoded with executable instructions which, when executed, cause the one or more processors to perform actions described herein. In some examples, the synchronization circuitry 302 and trigger circuitry 304 are implemented using one or more field-programmable gate array (FPGA) devices.

The synchronization device may have an input, for example, a wired or wireless input for receipt of an indication of stimulation initiation from an stimulation reading probe, such as the stimulation reading probe 107 of FIG. 1. As described with reference to FIG. 1, the implanted stimulator may provide stimulation every period in some examples—e.g. once or more every period of time, which may be regular or irregular. In some examples, input circuitry (e.g. Input logic) may be provided, which may include, for example, one or more rectifiers, comparators, or other components for manipulating an input signal received from stimulation systems described herein, such as from stimulation reading probe 107 of FIG. 1. The input logic may provide an indication of stimulation when a threshold magnitude of voltage and/or current is exceeded at the input. The threshold may be adjusted by a user as described herein. For example, an input signal from a stimulation system may be provided to a diode rectifier, which may serve to negate any negative voltage impulse from entering the circuitry, which may prevent and/or reduce damage to internal components. That signal may be provided to a comparator, where the voltage it is compared to may be based on a potentiometer controlled by the user. The comparator may provide a signal to the synchronization circuitry 302 as either a logic high or low (e.g. 3.3 V or 0 V), indicating that the stimulation has or hasn't started yet. The comparator may be controlled by a potentiometer to, for example, prevent and/or reduce noise being mistaken from stimulation. The output signal may be amplified before being output to the fMRI as a trigger.

The synchronization circuitry 302 may calculate an initial time of scan initiation at least in part by adding the period to a time the indication of stimulation initiation was received and subtracting a settling time during which a scanning system is configured to attain steady state.

The trigger circuitry 304 may provide a trigger to the scanning system to initiate a scan at the initial time. For example, the trigger may be a signal provided at the output of the synchronization device which may be provided to an MRI system (e.g. the fMRI system 102 of FIG. 1) to initiate a scan. The trigger may be provided, for example, to a control system of the imaging system.

In providing signals—e.g. indications of an initial or subsequent scan time, and/or triggers, the synchronization circuitry 302 and/or the trigger circuitry 304 may include or may be in communication with one or more amplifiers to amplify a signal to result in the indications and/or triggers described. For example, the trigger may be amplified to a level suitable for receipt and response by an imaging system.

The synchronization circuitry 302 may further calculate a next time of scan initiation at least in part by adding the period to the initial time. The trigger circuitry 304 may provide another trigger to the scanning system at the next time.

The time for each period, which may be irregular or regular, may be stored, for example, in memory 308, which may be implemented using any electronic storage—e.g. random access memory (RAM), read-only memory (ROM), solid state drives (SSDs), disk drive(s), etc. The memory 308 may be electronically accessible to the synchronization device, either through a wired or wireless connection. In some examples, the time for each period may additionally or instead be provided to an input of the synchronization device from the implanted stimulator and/or stimulation system.

In some examples, the synchronization device may implement a state machine (e.g. a state machine may be implemented using an FPGA), including by using the synchronization circuitry 302 and/or trigger circuitry 304 in some examples. One or more user input(s) may additionally be provided to the state machine (e.g. to the synchronization circuitry 302) which may be used in determining transitions between states in some examples.

In some examples, the synchronization device may include a display. The display may be in communication with the synchronization circuitry 302, trigger circuitry 304, output, or combinations thereof, and may display a remaining time until the initial stimulation time or a subsequent trigger time. In this manner, the synchronization device may display a countdown until each trigger time.

The power 306 may provide power to components of the synchronization device. In some examples, the power 306 may include a voltage regulator which may set an input voltage for one or more of the components—e.g. synchronization circuitry 302 and/or trigger circuitry 304.

Figure 4:
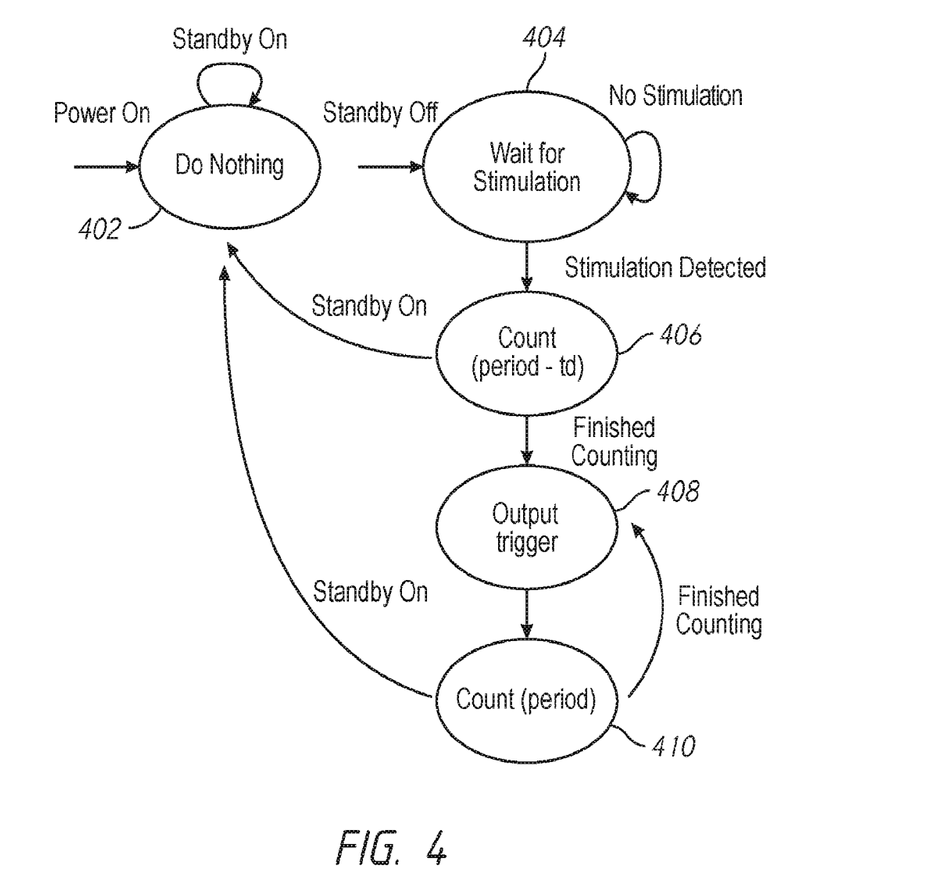
FIG. 4 is a state transition diagram for a state machine which may be implemented by examples of synchronization devices described herein.

FIG. 4 is a state transition diagram for a state machine which may be implemented by examples of synchronization devices described herein. For example, the state machine of FIG. 4 may be implemented by the synchronization device shown and described with reference to FIG. 3 in some examples. For example, the synchronization circuitry 302 and/or trigger circuitry 304 may be used to implement the state machine shown in FIG. 4. In some examples, instructions for implementing the state machine may be stored in a memory included in and/or accessible to the synchronization device.

The state machine in the example of FIG. 4 includes state 402, state 404, state 406, state 408, and state 410. In other examples, additional, fewer, and/or different states may be used.

In the example of FIG. 4, state 402 may be entered when power is turned on. State 402 may be a standby state. The synchronization device may not take any particular action responsive to a power on event, other than to be in the state 402 if a standby mode is on. As long as power and standby mode are on, the state 402 may be maintained, and the synchronization device may take no action.

When standby mode is exited, however, the synchronization device may transition to state 404. Standby mode may be exited, for example, responsive to a user input indicative of the exit of standby mode (e.g. by activation of a user accessible switch or other user input indicative of exiting standby mode). In some examples, the standby on/off indication may be provided by an imaging system, e.g. an fMRI system. For example, an operator may provide a start indication to the fMRI system and an exit standby signal could be provided responsive to that start indication, e.g. directly responsive to it or a predetermined time after the start indication. In some examples, the state 402 and state 404 may be a same state, such that the state 404 may be entered responsive to powering on the synchronization device. In state 404, the synchronization device may wait for an indication of stimulation. Note that when state 402 is separate from state 404, an indication of stimulation may have no effect on state 402, but may cause a change if received when the synchronization device is in state 404. In this manner, a user may control when information from a stimulation system is acted on by entering and/or exiting the standby mode.

In state 404, the synchronization device may await an indication of stimulation. Accordingly, in state 404, power may be on to the synchronization device, and the synchronization device may have exited a standby mode and be awaiting a stimulation indication from a stimulation system, such as from the stimulation reading probe 107 of FIG. 1. On receipt of the indication of stimulation (e.g. on detection of stimulation), the synchronization device may enter state 406. In state 406, the synchronization device may calculate and count to an initial trigger time. Accordingly, the state 406 may be an initial trigger calculation state. For example, the synchronization device may count for an amount of time equal to a period of stimulation minus a time (e.g. td) required to ensure an imaging system attained steady state. In some examples, the synchronization device may count down, while in other examples, the synchronization device may count up, and the count may in some examples be displayed on a display of, or in communication with, the synchronization device.

If, while in state 406, standby state (e.g. standby mode) is entered, the synchronization device may return to state 402 and/or state 404. So, for example, a user may avoid further operation of the imaging system under the control of the synchronization device by providing an input to the synchronization device indicative of standby state. If standby state is not entered, the count may complete, and the synchronization device may enter state 408. At state 408 the synchronization device may provide a trigger (e.g. an impulse) to an imaging system (e.g. FMRI system 102 of FIG. 1) to initiate a scan.

The synchronization device may then enter state 410. In state 410, the synchronization device may calculate and/or count a time to a next scan (e.g. subsequent trigger times). The state 410 may be a repetitive trigger state. Again, the synchronization device may count up, down, or both. Generally, the count will be for a period of time, which period may be stored in memory accessible to the synchronization device and/or communicated to the synchronization device. The next trigger time may be calculated by adding a period to a previous trigger time. If, while in state 410, standby state is entered, the synchronization device may transition instead to state 402 and/or state 404. If standby state is not entered, the synchronization device may transition to state 408 on completion of the count and provide another trigger (e.g. impulse) to initiate a next scan by an imaging system. State 408 and state 410 may repeat until standby is turned on and/or for a predetermined or communicated number of cycles.

Figure 5:
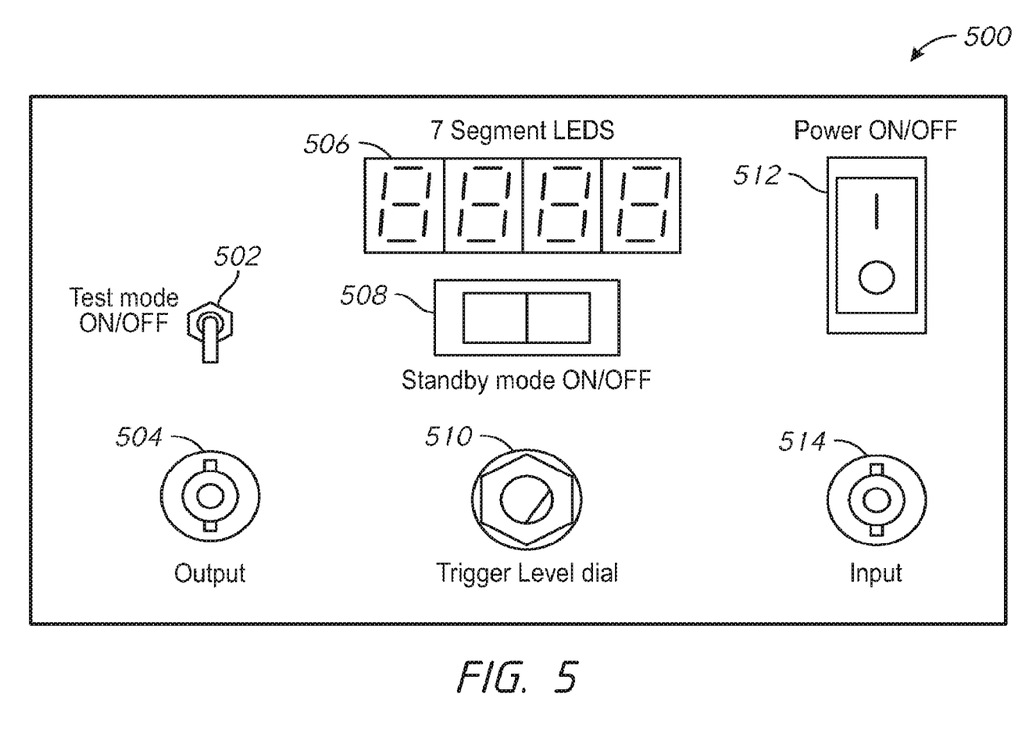
FIG. 5 is a schematic illustration of a synchronization device interface arranged in accordance with examples described herein.

FIG. 5 is a schematic illustration of a synchronization device interface arranged in accordance with examples described herein. The synchronization device 500 includes test mode input 502, output 504, display 506, standby mode input 508, trigger level input 510, power control 512, and input 514. The synchronization device 500 may have a housing, and in some examples the synchronization circuitry 302 and/or trigger circuitry 304 may be housed in the housing. For example, the synchronization device 500 may be used to implement and/or may be implemented by the synchronization device shown in FIG. 3 in some examples. While certain inputs and outputs are shown in FIG. 5, it is to be understood that in other examples, additional, fewer, and/or different inputs and outputs may be present.

The test mode input 502 may be implemented, for example, using a user accessible switch. In some examples, a toggle switch may be used. In other examples, a button, rocker switch, or other input may be used. In some examples, a touchscreen button or other touch-based input may be used. Entry into and out of test mode may cause the synchronization device 500 to implement and/or not implement a state machine, such as the state machine shown in FIG. 4. For example, in test mode, the synchronization device 500 may perform different functions for testing or other purposes. In some examples, test mode may cause the synchronization device to output what the synchronization circuitry may receive, which may aid in setting a threshold voltage for a comparator used to provide a signal indicative of stimulation.

The output 504 may provide a trigger, for example, to be provided to an imaging system as described herein. For example, the trigger provided in state 408 of FIG. 4 may be provided at output 504. The output 504 may be implemented using any wired or wireless output mechanism for communication with an imaging system. A BNC connector, coax, USB, HDMI, RS-232, wireless transmitter, or other output may be used.

The display 506 may display a time until a next trigger time, and may provide a count up and/or down. In some examples, the display 506 may be implemented using LEDs (e.g. 7-segment LEDs), and/or LCD, plasma, or other display devices. In some examples, the display 506 may be implemented using a separate device in communication with synchronization device 500.

The standby mode input 508 may allow a user (e.g. an operator, or in some examples another automated process) to have the synchronization device enter and/or exit standby mode. For example the standby mode input 508 may be implemented using a toggle switch, rocker switch, button, touchscreen interface, or other input. The standby mode input 508 may provide an indication to enter and/or exit standby mode which may be used to adjust behavior of the synchronization device, for example which of the states of FIG. 4 the synchronization device is in.

The trigger level input 510 may allow a user e.g. an operator, or in some examples another automated process) to have control over a threshold at which an indication of stimulation is determined to be received. For example, the synchronization device may compare a signal from a stimulation system (e.g. a voltage and/or current signal) to determine that stimulation is occurring, beginning, and/or has occurred. In some examples, when a magnitude of the signal is greater than a threshold value, the synchronization device may determine stimulation has occurred (or is occurring) and may proceed (e.g. may enter state 406 of FIG. 4). The trigger level input 510 may be provided to allow adjustment of such a threshold. For example, a dial may be used, which may control an electronic component, such as a potentiometer, or in some examples, a user may program the synchronization device (e.g. in hardware, software, and/or firmware) to utilize a particular threshold.

The power control 512 may allow a user (e.g. an operator, or in some examples another automated process) to turn power on and off to the synchronization device. For example, power on may cause the synchronization device to enter state 402 of FIG. 4. The power control 512 may couple and/or decouple the power 306 from the device of FIG. 3 in some examples. A rocker switch, toggle switch, button, or touchscreen interface may be used in some examples.

The input 514 may receive a signal from a stimulation system. Any variety of input may be used, including but not limited to, BNC connector, coax, USB, RS-232, or wireless receiver. The input received at input 514 may be examined to determine that stimulation has occurred and/or is occurring.

The collection of inputs and outputs shown in FIG. 5 is exemplary only, and it is to be understood that the inputs and/or outputs may be implemented using other input and/or output devices and that additional, fewer, and/or different inputs and outputs may be used in other examples.

Figure 6:
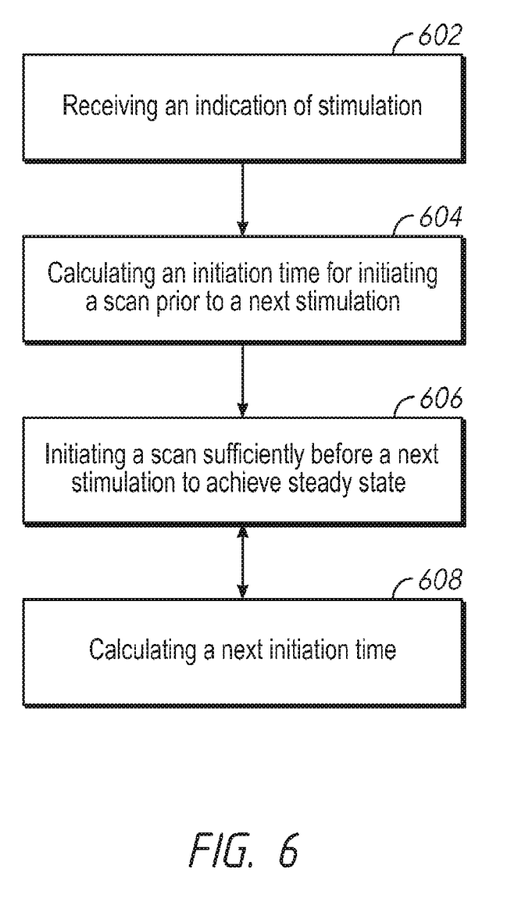
FIG. 6 is a flowchart illustrating a method arranged in accordance with examples described herein.

FIG. 6 is a flowchart illustrating a method arranged in accordance with examples described herein. The method includes receiving an indication of stimulation 602, calculating an initiation time for initiating a scan prior to a next stimulation 604, initiating a scan sufficiently before a next stimulation to achieve steady state 606, and calculating a next initiation time 608. Systems and synchronization devices described herein may be used to perform the method shown in FIG. 6.

The example method of FIG. 6 begins with receiving an indication of stimulation 602. The indication of stimulation may be received by a synchronization device from a stimulation system, such as the synchronization device 110 and implanted stimulator 106 of FIG. 1. As described herein, the indication of stimulation may be a separate signal provided by the stimulation system and/or may be a monitored signal of the stimulation system (e.g. a stimulation voltage and/or current magnitude being greater than a threshold).

Responsive to receiving an indication of stimulation 602, synchronization devices described herein may begin calculating an initiation time for initiating a scan prior to a next stimulation 604. As described, the initiation time may be calculated, for example, by adding a period to the time the indication of stimulation was received and subtracting a settling time of the imaging system. The next stimulation may be a next time when a patient is stimulated by a stimulation system, e.g. an implanted stimulator. As described herein, the stimulation system may stimulate the patient every period. The periods may be regular or irregular. The calculation may be performed by an electronic timer. The electronic timer may be implemented using synchronization circuitry described herein.

This allows the system to be initiating a scan sufficiently before a next stimulation to achieve steady state 606. The system may be an imaging system, such as an fMRI system, and the scan may be an fMRI scan in some examples. By providing a trigger in some examples to an imaging system at the initiation time, the imaging system may begin scanning with sufficient time to achieve steady state before a next stimulation. For example, a duration between an initiation time and a stimulation time may be sufficient for the imaging system (e.g. the fMRI system) to achieve steady state.

During the time in between the initiation time and the next stimulation time, the imaging system may perform one or more dummy scans.

Synchronization devices described herein may begin calculating a next initiation time 608 following the first initiation time. In some examples, the next initiation time may be calculated by adding a period to the previous initiation time (e.g. trigger time). The calculation may be performed by an electronic timer, which may be implemented by synchronization circuitry described herein. A next scan may be initiated (e.g. by providing another trigger signal) one or more periods after the initiation time calculated in calculating an initiation tune for initiating a scan prior to a next stimulation 604. The time one period after the initiation time may be prior to a next stimulation time when the patient may again be stimulated by a stimulation system (e.g. Implanted stimulator). During the time between one period after the initiation time (e.g. the next initiation time) and the next stimulation time, the imaging system may perform one or more dummy scans.

From the foregoing it will be appreciated that, although specific embodiments of the invention have been described herein for purposes of illustration, various modifications may be made without deviating from the spirit and scope of the invention.

What is claimed is:

1. A device comprising:
    an input configured to receive an indication of stimulation initiation from an implanted stimulator, the implanted stimulator configured to provide stimulation every period;
    synchronization circuitry configured to calculate an initial time of scan initiation at least in part by adding the period to a time the indication of stimulation initiation was received and subtracting a settling time during which a scanning system is configured to attain steady state; and
    trigger circuitry configured to provide a trigger to the scanning system to initiate a scan at the initial time.

2. The device of claim 1, wherein the synchronization circuitry is further configured to calculate a next time of scan initiation at least in part by adding the period to the initial time; and
    wherein the trigger circuitry is further configured to provide another trigger to the scanning system at the next time.

3. The device of claim 1, wherein the synchronization circuitry is provided in a field programmable gate array (FPGA) device.

4. The device of claim 1, further comprising a display configured to display a remaining time until the initial time.

5. The device of claim 1, wherein the device is configured to implement a state machine, and wherein a first state comprises a standby state, the device further comprising a second input configured to receive an indication to exit standby state, and wherein the synchronization circuitry is configured to calculate the initial time responsive to receipt of the indication of stimulation when the device has exited the standby state.

6. The device of claim 5, wherein the second input comprises a user accessible switch.

7. The device of claim 5, wherein a second state comprises an initial trigger calculation state during which the synchronization circuitry is configured to calculate the initial time, and wherein a third state comprises a repetitive trigger state during which the synchronization circuitry is configured to calculate next trigger times by adding the period to a previous trigger time.

8. The device of claim 1, further comprising a memory configured to store the period.

9. A method comprising:
    initiating a functional magnetic resonance imaging scan (an fMRI scan) of a patient with a functional magnetic resonance imaging system (an fMRI system) at an initiation time prior to a stimulation time when the patient is stimulated by an implanted stimulator, wherein the implanted stimulator is configured to stimulate the patient every period, and wherein a duration between the initiation time and the stimulation time is sufficient for the MRI system to achieve a steady state; and
    initiating another fMRI scan of the patient one period after the initiation time.

10. The method of claim 9 further comprising performing dummy scans with the fMRI system at a time between the initiation time and the stimulation time.

11. The method of claim 9, wherein the one period after the initiation time is prior to a second stimulation time when the patient is again stimulated by the implanted stimulator.

12. The method of claim 11 further comprising performing dummy scans with the fMRI system at a time between the one period after the initiation time and the second stimulation time.

13. The method of claim 9, further comprising receiving indication of an initial stimulation time from the implanted stimulator and calculating, using an electronic timer, the initiation time at least in part by adding the period to the initial stimulation time and subtracting a settling time during which the fMRI is configured to achieve the steady state.

14. The method of claim 13, further comprising providing a trigger signal from the electronic timer to the fMRI system at the initiation time.

15. The method of claim 14, further comprising counting, with the electronic timer, the period, and providing another trigger signal from the electronic timer to the fMRI system at the one period after the initiation time.

16. A system comprising:
    a functional magnetic resonance imaging system (an fMRI system), the fMRI system configured to provide fMRI scans of a patient;
    a stimulation system configured to stimulate the patient; and
    a synchronization device, the synchronization device configured to trigger the fMRI system to initiate at least one of the fMRI scans at a time prior to simulation of the patient by the stimulation system, such that the fMRI system attains steady state prior to the stimulation of the patient by the stimulation system.

17. The system of claim 16, wherein the fMRI system is configured to provide at least one dummy scan prior to attaining the steady state.

18. The system of claim 16, wherein the synchronization device is configured to receive an initial indication of stimulation from the stimulation system, and wherein the synchronization device is configured to determine a first trigger time by adding a period of the simulations provided by the stimulation system to a time of the initial indication and subtracting a settling time during which the fMRI system is configured to attain the steady state.

19. The system of claim 18, wherein the synchronization device is configured to provide a trigger signal to the fMRI system to initiate a scan at the first trigger time.

20. The system of claim 18, wherein the synchronization device is configured to determine subsequent trigger times by adding multiples of the period to the first trigger time.

21. The system of claim 20, wherein the synchronization device is configured to provide trigger signals to the fMRI system to initiate scans at the subsequent trigger times.

* * * * *